(12) United States Patent
Hartzell et al.

(10) Patent No.: US 8,236,244 B2
(45) Date of Patent: *Aug. 7, 2012

(54) MICRO-PIXELATED FLUID-ASSAY STRUCTURE WITH ON-BOARD ADDRESSABLE, PIXEL-SPECIFIC FUNCTIONALIZATION

(75) Inventors: John W. Hartzell, Camas, WA (US); Pooran Chandra Joshi, Vancouver, WA (US); Paul J. Schuele, Washougal, WA (US)

(73) Assignee: Sharp Laboratories of America, Inc., Camas, WA (US)

( * ) Notice: Subject to any disclaimer, the term of this patent is extended or adjusted under 35 U.S.C. 154(b) by 283 days.

This patent is subject to a terminal disclaimer.

(21) Appl. No.: 11/827,173

(22) Filed: Jul. 10, 2007

(65) Prior Publication Data

US 2008/0085564 A1     Apr. 10, 2008

Related U.S. Application Data

(60) Provisional application No. 60/849,875, filed on Oct. 6, 2006.

(51) Int. Cl.
*G01J 3/00* (2006.01)
(52) U.S. Cl. ....... 422/82.05; 422/62; 422/129; 422/400; 385/12; 385/129; 435/6; 435/287.1; 435/288.7; 356/317; 356/440; 506/9
(58) Field of Classification Search .................. None
See application file for complete search history.

(56) References Cited

U.S. PATENT DOCUMENTS

| | | | |
|---|---|---|---|
| 5,143,854 A | 9/1992 | Pirrung et al. | |
| 5,514,501 A * | 5/1996 | Tarlov | ............... 430/5 |
| 6,093,302 A | 7/2000 | Montgomery | |
| 6,197,503 B1 | 3/2001 | Vo-Dinh et al. | |
| 6,280,595 B1 | 8/2001 | Montgomery | |
| 6,403,317 B1 | 6/2002 | Anderson | |
| 6,551,784 B2 * | 4/2003 | Fodor et al. | ........ 435/6 |

(Continued)

FOREIGN PATENT DOCUMENTS

WO   WO 9210092   6/1992

OTHER PUBLICATIONS

McGall, et al., Jun. 4, 1997, *Journal of the American Chemical Society*, 119(22).

(Continued)

*Primary Examiner* — Sally Sakelaris
(74) *Attorney, Agent, or Firm* — David C. Ripma, Esq.; Jon M. Dickinson

(57) ABSTRACT

A digitally-addressable, pixelated, DNA fluid-assay, active-matrix micro-structure formed, utilizing low-temperature TFT and Si technology, on a substrate preferably made of glass or plastic, and including at least one pixel which is defined by (a) an addressable pixel site, (b) a sensor home structure disposed within that site for receiving and hosting a functionalized assay site possessing a DNA oligonucleotide probe, and (c) an addressable, pixel-site-specific, energy-field-producing functionalizer (preferably optical) operable to functionalize such a probe on the assay site. Each pixel may also include a pixel-integrated optical detector. Further disclosed are related methodology facets involving (1) the making of such a micro-structure (a) in a precursor form (without a functionalized probe), and thereafter (b) in a finalized/functionalized form (with such a probe), and (2) the ultimate use of a completed micro-structure in the performance of a DNA assay.

2 Claims, 3 Drawing Sheets

U.S. PATENT DOCUMENTS

| | | | |
|---|---|---|---|
| 6,605,796 | B2 | 8/2003 | Brandinger et al. |
| 6,794,052 | B2 * | 9/2004 | Schultz et al. ............... 428/500 |
| 6,860,939 | B2 | 3/2005 | Hartzell |
| 6,985,655 | B2 | 1/2006 | Yamamoto |
| 7,125,451 | B2 | 10/2006 | Hartzell |
| 7,128,783 | B2 | 10/2006 | Hartzell |
| 7,135,070 | B2 | 11/2006 | Hartzell |
| 7,156,916 | B2 | 1/2007 | Hartzell |
| 7,163,822 | B2 * | 1/2007 | Yazawa et al. ............ 435/287.2 |
| 2003/0035109 | A1 | 2/2003 | Hartwich et al. |
| 2003/0219196 | A1 * | 11/2003 | Weng et al. .................... 385/17 |
| 2005/0063870 | A1 * | 3/2005 | Fukushima et al. ....... 422/82.05 |
| 2007/0072169 | A1 | 3/2007 | Peyvan et al. |

OTHER PUBLICATIONS

Arntz et al. 2003. "Label-free protein assay based on a nanomechanical cantilever array." *Nanotechnology*. 14:86-90 (5 pp).

Jacobson et al. 1985. "Functionalized Congeners of Adenosine: Preparation of Analogues with High Affinity for $A_1$-Adenosine Receptors" *J. Med. Chem*. 28:1341 (1 p, abstract only).

Noda et al. "Development of Photolithography System with Liquid Crystal Device as Active Mask for Synthesizing DNA Chips", Proceedings of the Japan Society of Mechanical Engineers, Kanto Branch, the Japan Society for Precision Engineering, Ibaraki Conference, 2003, vol. 2003, p. 201-202. Japan.

USPTO Office Action, U.S. Appl. No. 11/827,335, dated Mar. 15, 2010, 20 pages total.

USPTO Office Action, U.S. Appl. No. 11/827,335, dated Aug. 11, 2010, 16 pages total.

USPTO Office Action, U.S. Appl. No. 11/827,175, dated Jan. 3, 2011, 13 pages total.

USPTO Office Action, U.S. Appl. No. 11/827,174, dated Dec. 3, 2010, 14 pages total.

USPTO Office Action, U.S. Appl. No. 11/827,176, dated Jan. 3, 2011, 14 pages total.

USPTO Office Action, U.S. Appl. No. 11/888,491, dated Jun. 25, 2010, 11 pages total.

USPTO Office Action, U.S. Appl. No. 11/888,491, dated Nov. 15, 2010, 8 pages total.

USPTO Office Action, U.S. Appl. No. 11/827,335, dated Apr. 12, 2011, 13 pages total.

USPTO Office Action, U.S. Appl. No. 11/827,175, dated May 31, 2011, 11 pages total.

USPTO Office Action, U.S. Appl. No. 11/827,174, dated Apr. 11, 2011, 14 pages total.

USPTO Office Action, U.S. Appl. No. 11/827,176, dated May 31, 2011, 10 pages total.

USPTO Office Action, U.S. Appl. No. 11/888,491, dated Apr. 12, 2011, 11 pages total.

* cited by examiner

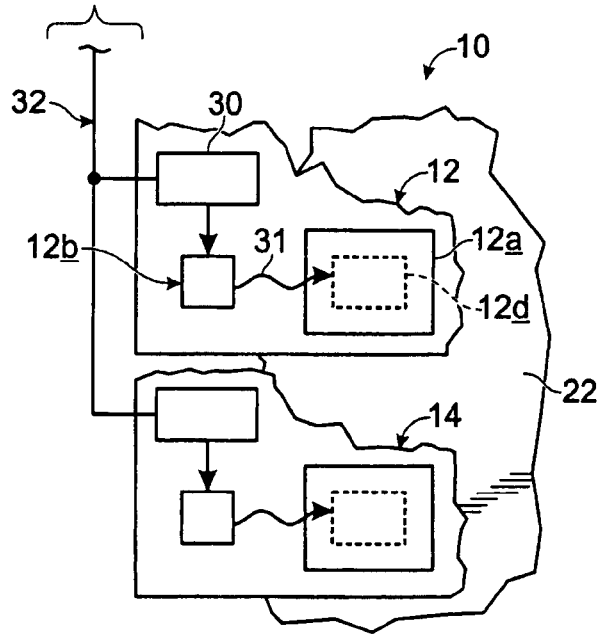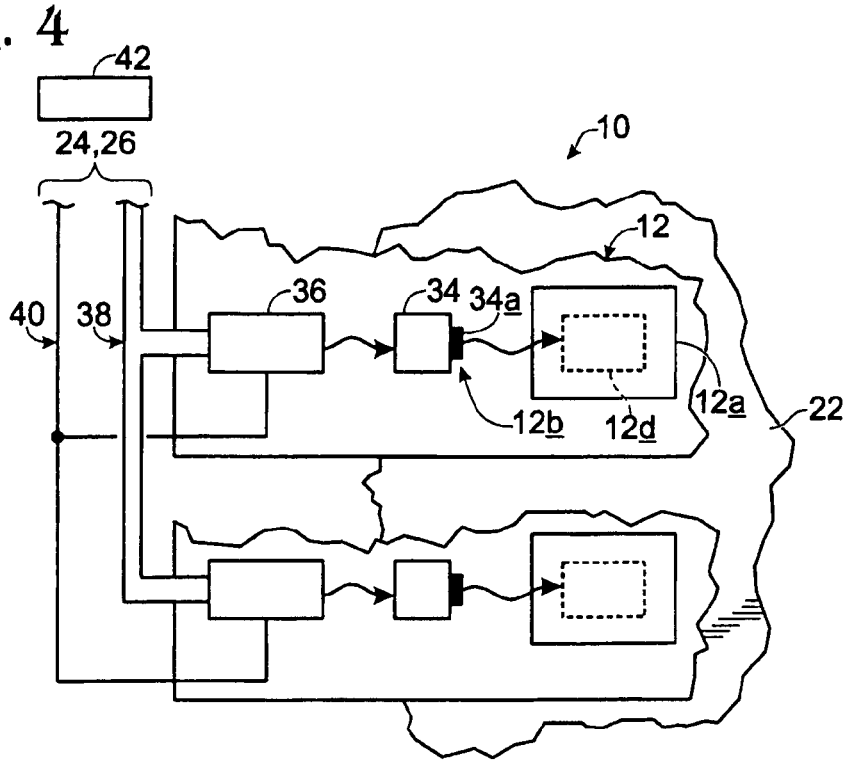

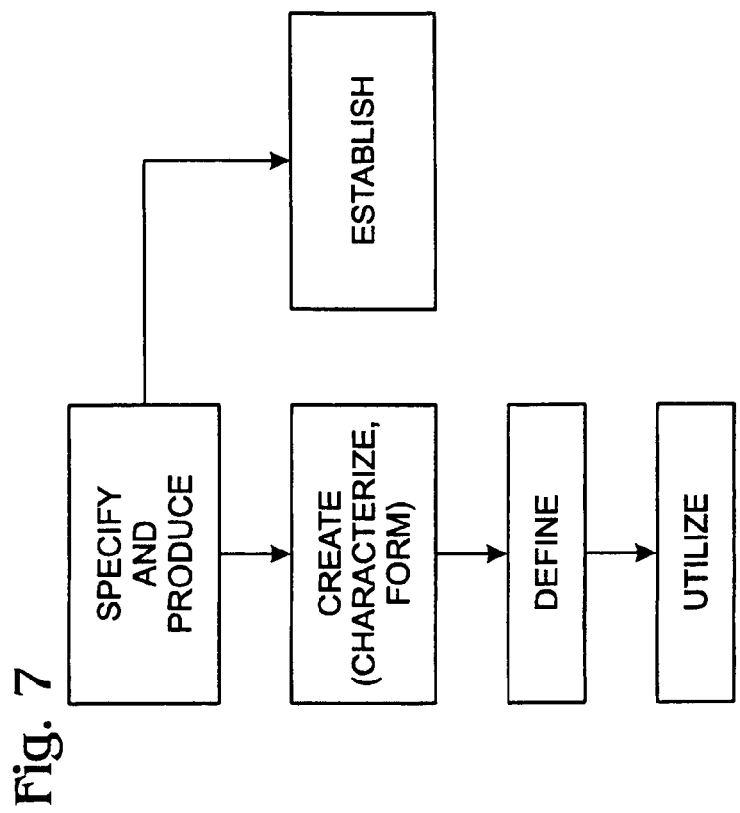
Fig. 7
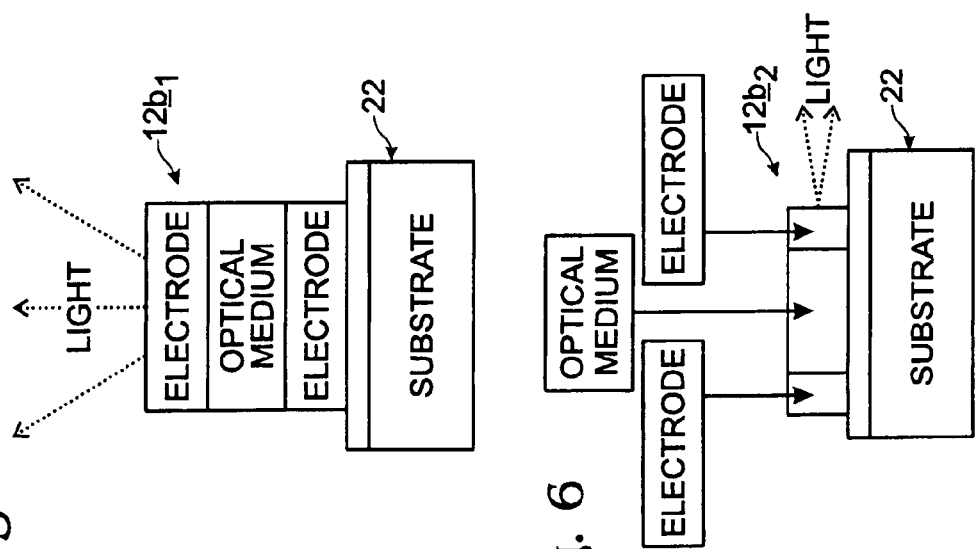
Fig. 5
Fig. 6

MICRO-PIXELATED FLUID-ASSAY STRUCTURE WITH ON-BOARD ADDRESSABLE, PIXEL-SPECIFIC FUNCTIONALIZATION

CROSS REFERENCE TO RELATED APPLICATION

This application claims filing-date priority to currently pending U.S. Provisional Patent Application Ser. No. 60/849,875, filed Oct. 6, 2006, for "Micro-Pixelated Array Assay Structure and Methodology". The entire disclosure content of that prior-filed provisional case is hereby incorporated herein by reference.

BACKGROUND AND SUMMARY OF THE INVENTION

This invention relates to DNA assay technology. More particularly, it relates to a new and unique, digitally-addressable, pixelated, thin-film-based, DNA fluid-assay micro-structure, and to associated methodologies for making and thereafter using such micro-structure.

DNA sensor, or assay, technology, in general terms, offers great promise for a host of scientifically, medically, and other diagnostically important studies and detection practices. However, this technology is shadowed by a number of important drawbacks to which the present invention directs focused, remedial attention.

Current DNA micro-assay structures typically take the form of substrate-supported fields, or arrays, of synthesized oligonucleotide probes. These probes, when formed, and when readied for use with appropriate, selected sensitivities to predetermined oligonucleotide compounds, are exposed to applied fluid material of DNA interest, and are thereafter prompted to fluoresce under the influence of an illuminating external laser, thereby to produce a "viewable", image-capturable fluorescence pattern from which an assay interpretation is made utilizing various special templates which are required in order for one to obtain an appropriate image analysis. This imaging and template-based image-analyzing is quite time-consuming, expensive, and prone to inaccuracy.

For many reasons which are well known to those generally skilled in the relevant art, conventional micro-assay DNA probe structures are typically single-use in nature, are complex and very costly to manufacture, and are, on balance, and as was just suggested above, ultimately quite expensive to use. These today-conventional, chip-like micro-array structures, additionally, are often frustratingly inaccurate in performance because of many false-positive responses produced during assays. Further, assays performed with these current structures can be very slow to yield assay results, often taking many hours, and often "overnight", to do this. Consequently, they do not lend themselves to rapid, high-throughput performance.

In addition to these several, above-mentioned prior-art drawbacks and disappointments, the assortment of equipment required for DNA assay-structure manufacturing and ultimate use is large, and the relevant, required equipment is usually bulky and expensive. In this setting, convenient and desired portability for conventional DNA assay practice in a non-centralized fashion is just not practical or economically possible.

The present invention dramatically addresses these prior-art drawbacks and constraints.

Featured by the invention are a unique, digitally-addressable, pixelated, thin-film-based, DNA fluid-assay, active-matrix micro-structure, and the related making and using methodologies, wherein, using very conventional, basic wafer-scale nano-processing and thin-film techniques, mentioned somewhat more fully below, and which techniques are well known to those skilled in the art, an array of individually digitally addressable, specialized micro-pixels, or pixels, is developed on a supporting substrate, preferably made of glass or plastic, as will be explained more fully below.

Preferably further, and in the above context, the invention takes the form of a relatively inexpensive, consumer-level-affordable DNA assay structure which features a low-cost substrate that will readily accommodate low-cost, and preferably "low-temperature-condition", fabrication thereon of substrate-supported DNA matrix-pixel "components". "Low temperature" is defined herein as a being a characteristic of processing that can be done on substrate material having a transition temperature (Tg) which is less than about 850° C., i.e., less than a temperature which, if maintained during sustained material processing, would cause the subject material to lose dimensional stability.

Accordingly, while the DNA matrix-pixel technology of this invention, if so desired, can be implemented on more costly supporting silicon substrates, the preferred supporting substrate material is one made of lower-expense glass or plastic materials. The terms "glass" and "plastic" employed herein to describe a preferred substrate material should be understood to be referring also to other suitable "low-temperature materials. Such substrate materials, while importantly contributing on one level to relatively low, overall, end-product cost, also allow specially for the compatible employment, with respect to the fabrication of supported pixel structure, of low-temperature processes and methods that are based on amorphous, micro-crystal and polysilicon thin-film-transistor (TFT) technology. In particular, these substrate materials uniquely accommodate the use of the just-mentioned low-temperature TFT technology in such a way that electrical, mechanical and electromagnetic field-creating devices—devices that are included variously in the DNA assay micro-structure of the invention—can be fabricated in a "thin-film manner" simultaneously in a process flow which is consistent with the temperature tolerance of such substrate materials.

Regarding the preference herein for the use of low-temperature TFT technology, and briefly describing aspects of that technology, low-temperature TFT devices are formed through deposition processes that deposit silicon-based (or other-material-based, as mentioned below herein, and as referred to at certain points within this text with the expression "etc.") thin-film semiconductor material (which, for certain applications, may, of course, later be laser crystallized to establish certain desired characteristics). This is quite different from classic silicon CMOS device technology that utilizes a single-crystal silicon-wafer bulk material as its semiconductor material. While the resulting TFT devices may not have the switching speeds and drive capabilities of transistors formed on single-crystal substrates, TFT transistors (electronic switching devices) can be fabricated cheaply with a relatively few number of process steps. Further, thin-film deposition processes permit low-temperature TFT devices to be formed on alternate substrate materials, such as transparent glass substrates, for use, as an example, in liquid crystal displays. In this context, and speaking specifically and illustratively at this point about silicon, it will be understood that low-temperature TFT device fabrication may variously involve the use typically of amorphous Si (a-Si), of micro-crystalline Si, and or of polycrystalline Si formed by low-temperature internal crystalline-structure processing of amorphous Si. Such processing is described in U.S. Pat. No. 7,125,451 B2, the contents of which patent are hereby incorporated herein by reference.

For the sake simply of convenience of expression regarding the present invention, and in order to emphasize the "low-temperature", thin-film-based formation possibility which is associated with the invention in its preferred form, all aspects of assay-matrix pixel fabrication and resulting structure are referred to herein in the context and language of "low-temperature silicon, etc. on glass or plastic" construction, and also in the context and language of "low-temperature TFT and Si technology".

Returning attention now to earlier discussion herein, the term "active-matrix" refers to a pixelated structure in which each pixel is controlled by some form of a switching device. Each of these pixels, in what can be thought of as its precursor condition, and with reference to a preferred embodiment of the invention, includes a site readied for hosting at least one, selected, still-to-be-built, DNA oligonucleotide probe, and at least one, adjacent, digitally addressable, pixel-specific, preferably thin-film structure referred to herein as an energy-field-producing functionalizer (and also as an electromagnetic field-creating structure), preferably taking the form of a light source (an optical source) operable at a predetermined wavelength and power level. Such a functionalizer performs as an optical-power energizer/illuminator/field-creator during, and even after, the process of functionalizing a pixel beyond its precursor condition. In particular, such a functionalizer in each pixel is selectively activatible both (a) to play an important energizing role in the post-precursor building (pixel-functionalizing) of a pixel-site-specific oligonucleotide probe, and (b) additionally later, and preferably, to play a key, supplementary role in illuminating the site of that probe with an electromagnetic light field to cause DNA material which has attached to it during a DNA assay to fluoresce during the carrying out of a DNA fluid-assay.

Also included within the site of each pixel (i.e., pixel integrated), in the pixel's precursor condition, is at least one fully pixel-integrated, individually digitally-addressable, pixel-specific optical detector which is employed during a DNA assay to "read" any fluorescence response (created by DNA assay material which has attached to the associated oligonucleotide probe) when that attached-to probe is illuminated by an associated functionalizer.

In the fully-functionalized (i.e., non-precursor) condition of each pixel, there is at least one fully formed, selected, oligonucleotide probe which has been built (i.e., functionalized) with the aid of the mentioned, appropriate, digitally-addressable, pixel-specific functionalizer.

As will become apparent, the "pixel-on-board natures" of the digitally-addressable, pixel-specific functionalizers and optical detectors (a) uniquely address the several above-mentioned issues associated with the prior art, and (b) sharply distinguish this invention from that art.

These and other features and advantages which are offered by the present invention will become more fully recognized as the detailed description thereof which follows below is read in conjunction with the associated drawings.

DESCRIPTION OF THE DRAWINGS

FIG. 1 is employed herein to show several different styles, or modifications, of internal pixel construction.

FIG. 3 is a fragmentary, block/schematic diagram illustrating one general embodiment of a functionalizer which is included in the structures shown in FIGS. 1 and 2, and which takes the preferable form of a fully pixel-integrated, transistor-based, optical-medium-style light source.

FIG. 4 is similar to FIG. 3, except that it shows another general embodiment of a functionalizer made in accordance with the invention, here taking the form of an output port in an optical beam device which is supplied, via a pixel-integrated optical switching device, with a switchable flow of light furnished by a substrate-supported optical beam structure which is coupleable with an appropriate off-pixel light supply.

FIG. 5 is related to FIG. 3, and shows schematically the features of a vertical-stack-style optical-medium light-source functionalizer.

FIG. 6 is similar to FIG. 5, except that it shows schematically the features of a horizontal-style optical-medium light-source functionalizer.

FIG. 7 is a simplified, block/schematic diagram generally illustrating the architecture of methodology which forms part of the present invention.

DETAILED DESCRIPTION OF THE INVENTION

Figure 1:
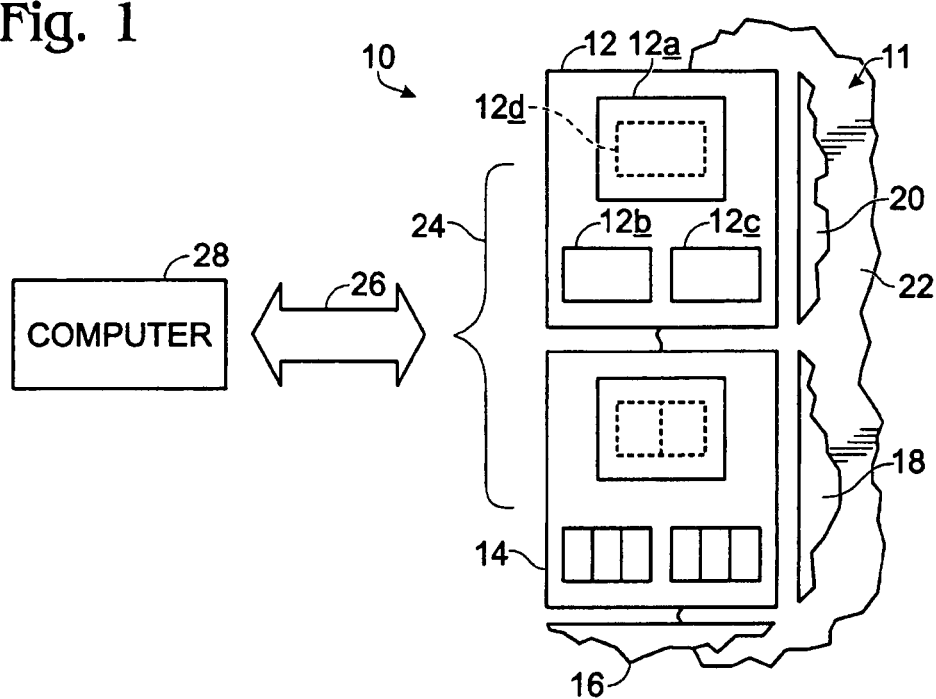
FIG. 1 is a simplified, block/schematic view of a portion of a digitally-addressable, thin-film-based, pixelated, fluid-assay, active-matrix micro-structure formed preferably on a glass or plastic supporting substrate utilizing the above-mentioned low-temperature TFT and Si technology, useable ultimately in the making of a DNA fluid-assay, and constructed in accordance with a preferred embodiment of, and manner of practicing, the present invention.

Turning now to the drawings, and referring first of all to FIG. 1, indicated generally at 10 is a fragmentary portion of a digitally-addressable, thin-film-based, pixelated, fluid-assay, active-matrix micro-structure which takes the form herein of a column-and-row array 11 of plural, individually addressable micro-pixels, or pixels, such as those shown at 12, 14, 16, 18, 20, formed, as will shortly be described (but generally utilizing low-temperature TFT and Si technology as mentioned above), on an appropriate substrate 22 which is preferably made of glass or plastic. In terms of individual-pixel digital addressability, collectively a bracket 24 and a double-ended, broad arrow 26 represent a communication connection (an addressing connection) between the pixels in micro-structure 10 and a remote computer shown in block form at 28.

In the particular embodiment of micro-structure 10 which is illustrated in FIG. 1, and notwithstanding the obvious visual difference which appears between fully illustrated pixels 12, 14—a difference which will be explained below—each of the mentioned pixels, for the purpose of the present-embodiment description of the invention, is deemed to be essentially identical to each other pixel, although, as will later be explained herein, this is not necessarily a requirement of the present invention. This "not-necessarily" last statement is based upon our clear understanding that there are various applications wherein differentiated pixels created in a single micro-structure array are desirable. Some of these differentiated-pixel concepts will be mentioned later herein.

The visual difference between pixels 12 and 14 is, of course, intentional, and has been employed herein for the purpose of utilizing the modified image of pixel 14 in FIG. 1 to describe (later herein) several useful, pixel-internal, micro-structure modifications which are accommodated readily by the present invention.

In general terms, and using pixel 12 as an illustration to explain the basic construction of each of the pixels shown in array 11, included in pixel 12, which is also referred to herein as a pixel site, are several, fully integrated, pixel-specific components, or substructures, including a sensor home structure 12a, a functionalizer 12b, and an optical detector 12c, also referred to herein as a response detector. It should be understood that pixel 12, as well as the several, integrated, pixel-specific components (substructures) therein just mentioned, are illustrated herein merely schematically in the forms of various sizes and shapes of rectangles. The actual sizes and shapes of all of these structures and substructures are entirely matters of user selection. In array 11, each pixel has a size of about 500×500-µm. Preferably, thin-film processing is employed wherever appropriate in all aspects of pixel construction. This having been said, we here point out that the text which follows will sometimes, but not always, re-refer to thin-film processing practices.

Figure 2:
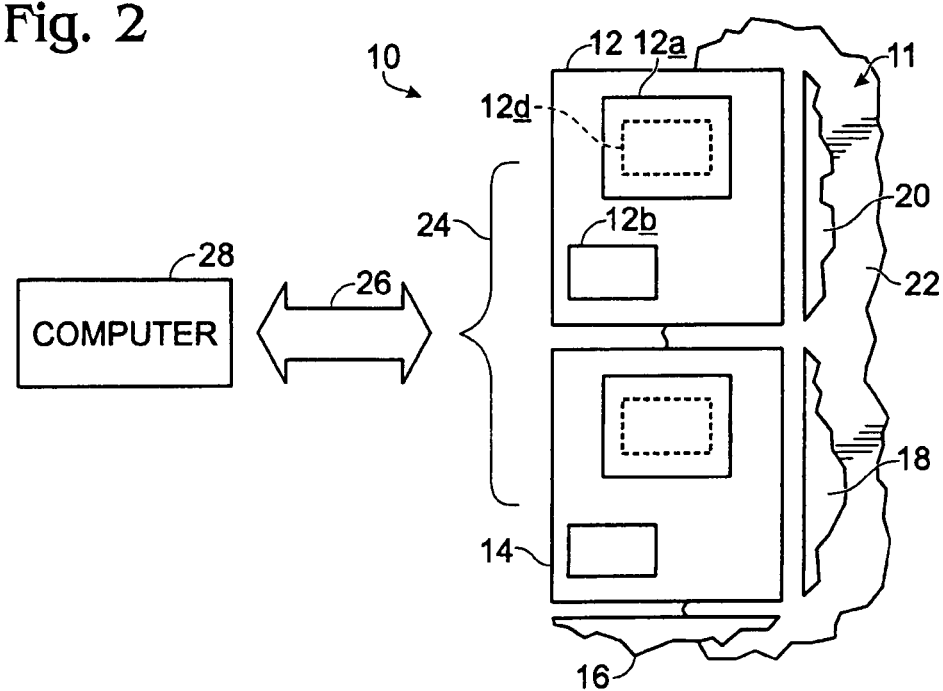
FIG. 2 is similar to FIG. 1, except that it shows another modified form of the invention wherein created pixel sites, or pixels, do not include pixel-specific optical detectors.

It should further be understood that FIGS. 1 and 2 in the drawings, as well as FIGS. 3 and 4 shortly to be described, are presented in manners which allow them to represent two different micro-structure "conditions", one of which is referred to herein as a "precursor" condition, and the other of which is referred to as a "finished", "finalized" or "functionalized" condition.

With this in mind, and from the "precursor" point of view, indicated in FIG. 1 by a dashed-line rectangle 12d, is a hosting, or home, site (another substructure) within sensor home structure 12a on which, as will shortly be described, a DNA oligonucleotide probe will ultimately be formed to place pixel 12 in a functionalized condition. This same dashed-line rectangle, from a "finished", "finalized" or "functionalized" point of view, represents the actual structure of such a fully created (i.e., functionalized) probe, per se. The precursor condition of a pixel is that condition of the pixel wherein no oligonucleotide probe has been created. The functionalized condition of a pixel is that wherein such a probe has been created.

In terms of how the various pixels included in microstructure array 11 are formed to have their precursor conditions, and how, within each pixel, such as within pixel 12, the precursor substructures, such as substructures 12a, 12b, 12c, 12d, are formed, the fabrications of these substructures take place herein preferably utilizing, as much as possible, conventional, thin-film, photolithographic, materials-processing, practices, and specifically the low-temperature TFT and Si technology practices mentioned above, which are well known to those skilled in the art.

Accordingly, while the broad-level collaborative acts, or steps, of this invention which are involved in creating, generally, a pixel precursor architecture, such as that just described, are unique, the specific materials-processing techniques for creating the individual, physical precursor elements per se of the array and pixel structure so far described do not form any part of the present invention, and thus are not described herein in detail. Stated another way, the overall collaborative arrangements of high-level, preferred-embodiment, micro-structure-making steps, which steps may be expressed herein as (1) specifying and producing pixel sites in a plural-pixel-site array, (2) creating for and within each such site a pixel-site-specific, individually addressable and energizable, energy-field-producing functionalizer (referred to herein as being at least a part of "thin-film, digitally-addressable electronic switching structure", and preferably taking the form of a light source), (3) establishing an optical (or response) detector for and within each pixel site, and (4) defining for each pixel site a pixel-specific home structure possessing a site for hosting a to-be-created oligonucleotide probe, are steps which, collectively, and as a cooperative whole, are unique in the art, whereas the specific manners of implementing these steps as individuals may be, and preferably are, entirely conventional.

The additional, post-precursor practice, however, of creating a DNA oligonucleotide probe, which additional practice involves moving beyond the precursor condition of a pixel to the fully functionalized, or finished, condition for that pixel, is thoroughly unique in the specifics of its implementation, insofar as the use of energizing light (as a functionalizing medium) is employed in the process of probe fabrication, also referred to herein as probe synthesizing.

The precursor-formation steps of specifying and producing pixels, and of defining sites within these pixels for hosting oligonucleotide probes, principally involve conventional, substrate-landscape-planning "layout" procedures. The precursor-formation steps of creating functionalizers/field-creators, and of establishing optical detectors, involve conventional thin-film fabrication practices of the type generally mentioned briefly above. The "additional practice" step relating to pixel-functionalizing, in the form of creating/fabricating a hosted DNA oligonucleotide probe, involves employing the precursor-created functionalizers as fully pixel-integrated, pixel-specific, light-energizing sources to be employed centrally in the actual forming of such hosted probes.

Referring now collectively to FIGS. 1 and 3-6, inclusive, sensor home structure 12a is a space defined within pixel 12 which, for a pixel size such as that mentioned earlier herein, might occupy an area of about 100×100-µm. Probe hosting site 12d, which is defined (as a singularity in the array embodiment now being described) within home structure 12a, might typically occupy an area which is either the same as, or slightly less than, that of structure 12a. Site 12d is shown schematically with a smaller size herein in order to be able to point out clearly its presence within the confines of pixel 12 and home structure 12a.

Functionalizer, electromagnetic-field-creating structure 12b takes the form herein preferably of one of two different specific types of individually digitally-addressable light sources with respect to which the energy field produced is an optical energy field. One of these forms is that of a thin-film, transistor-based (i.e., transistor-switchable, or electronically-switchable) optical medium which operates as a completely on-board, pixel-specific device. The other form is that of an output port in an optical beam device which is suitably coupled, as will be more fully discussed shortly, with a substrate-supported optical beam structure which, in turn, is operatively coupleable with what is referred to herein as an off-pixel light supply.

FIGS. 3, 5 and 6 relate to the mentioned transistor-switchable optical-medium type light source, and attention is thus now directed specifically to these three figures to be viewed in conjunction with FIG. 1. As illustrated in these figures, functionalizer 12b is constructed to have one of two different types, or styles, of relatively conventional, thin-film, transistor-switchable (electronically-switchable) optical media, each of which is selectively addressable and individually energizable via an appropriately connected, pixel-specific energizing transistor, such as the energizing transistor shown at 30 in FIGS. 3, 5 and 6.

FIG. 5 illustrates optical-medium functionalizer 12b as taking the form of a vertical-stack-style, transistor-energized (electronically-switchable) optical medium $12b_1$, whereas FIG. 6 illustrates optical-medium functionalizer 12b as taking the form of a horizontal-style, transistor-energized (electronically-switchable) optical medium $12b_2$. In both cases, and for reasons which will become apparent shortly, light coming from the pixel-established optical medium is directed appropriately toward home structure 12a, as is indicated generally by sinuous arrow 31 in FIG. 3. Also, in case of each style of optical medium, light from these two different kinds of optical media is generated with a wavelength lying in the range of about 280-nm to about 550-nm, and with a power level preferably residing in a range of about 10-nW/cm$^2$ to about 50-nW/cm$^2$.

Referring to the "optical medium" appearing in FIGS. 5 and 6, and mentioned above, this optical medium can be any suitable layer that emits light effective for the requisite functionalization process. This light is preferably in the UV range but may also be in the visible light range. The optical medium can be a single or multilayer film structure. Particularly, a multilayer stack may be engineered to tune and control the emitted wavelength and output power. The optical medium can be formed with one or several semiconductor film layers selected from a group including elemental or compound semiconductors. Examples of semiconductors materials include: Si, Ge, Zn (silicon, etc. materials). The optical medium may also be a dielectric matrix infused with quantum dots or nano-particles uniformly dispersed in the medium. Examples of dielectric, silicon, etc. materials include SiOx, SiOxNy, SiNx.

Appropriate, individually addressable, pixel-specific energizing connections for energizing the mentioned transistors, and thus for effecting the resulting emission of light, are supplied via suitable conductor structure, such as that shown generally at 32 in FIG. 3. This conductor structure forms part of the previously mentioned communication interconnection 24, 26 which exists between array 11 and an external computer, such as computer 28.

Fabrication of these just-discussed, two styles of transistor-energized (i.e., transistor-based) optical media, and of the communication (energizing) connections therefor, is accomplished preferably, as mentioned earlier herein, by well-known, conventional, thin-film manufacturing steps.

With attention turned now specifically to FIGS. 1 and 4, FIG. 4 illustrates schematically, that embodiment of the invention wherein the preferred-embodiment light-source functionalizer takes the form of an optical output port 34a in an otherwise conventional optical beam device 34. Beam device 34 is coupled optically, through a conventional, thin-film optical switching structure, or device, 36, to a conventional, thin-film optical beam structure 38. Beam structure 38 is suitably formed (conventionally) on the body of substrate 22.

As an aside comment here, and as will be well understood by those skilled in the relevant art, it is the presences of the mentioned transistor and switching structures in the pixels of this invention which make the matrix array of the invention an active matrix array.

Appropriate, otherwise conventional, thin-film electrical energizing connections are made to the pixel-specific optical switching devices, such as device 36, via a suitable electrical conductor structure 40 which is similar to previously mentioned conductor structure 32 shown in FIG. 3. Also, an appropriate and preferably conventional optical coupling is enabled between beam structure 38, and a suitable off-pixel, off-substrate light supply, such as that shown schematically by block 42 in FIG. 4. This light supply is appropriately associated operatively with a computer, such as computer 28. This optical coupling, or connection, which is provided for beam structure 38, collectively with conductor structure 40, forms parts of previously mentioned communication interconnection 24, 26.

When output light (an electromagnetic light field) is enabled from beam-device port 34a, this light, as derived from the mentioned off-pixel, off-substrate light supply 42, is directed toward the relevant, pixel-associated home structure, such as home structure 12a, with this output light possessing a wavelength lying in the range of about 280-nm to about 550-nm, and with a power level preferably lying in a range of about 10-nW/cm$^2$ to about 50-nW/cm$^2$.

Looking now particularly at pixel 14 in relation to the fact, pointed out earlier herein, that this pixel is shown differently in FIG. 1 than is pixel 12, pixel 14 has been drawn herein to help illustrate several different pixel-structure modifications which may be employed. These modifications relate to the specific substructures within pixel 14, including home structure 14a, functionalizer(s) 14b, optical (response) detector(s) 14c, and probe-hosting site(s) 14d.

More specifically, with respect to home structure 14a, overall hosting site 14d within this home structure is illustrated as including a pair of (representative plural) hosting sub-sites $14d_1$ and $14d_2$. Such plural, probe-hosting sub-sites may be employed to implement pixel structure, in an array made in accordance with the present invention, having different-material DNA assay capabilities, as, for example, by including (i.e., hosting) plural, different, specific DNA oligonucleotide probes—one each per hosting sub-site. It should also be understood that different, specific DNA oligonucleotide probes may be constructed on different pixels within the overall arrangement of array 11, thus to furnish yet another kind of option for creating a plural-functionality, plural-differentiated-probe, DNA assay micro-structure. Further, it should be understood that, while pixel 14 is illustrated with a pair of hosting sub-sites to accommodate two different kinds of DNA oligonucleotide probes, a different number of such hosting sub-sites could be incorporated within a single pixel if desired. A but more will be said about this possibility later herein in the context of mentioning micro-structure array fabrication possessing broad-band DNA assay capabilities.

In pixel 14, functionalizer 14b is illustrated as including three sub-functionalizers (field-creating structures) $14b_1$, $14b_2$ and $14b_3$. This has been done to illustrate the possibility, particularly applicable to a situation where different, specific DNA oligonucleotide probes are to be formed, for utilizing optical light-source functionalizers which operate at different optical wavelengths, and/or at different power levels, to accommodate the formations and assay-uses of different, pixel-specific DNA oligonucleotide probes.

Finally, pixel 14 is illustrated with an optical detector structure 14c which includes three sub-detector structures $14c_1$, $14c_2$ and $14c_3$. This illustrates the possibility of utilizing different-wavelength optical detectors to respond to different fluorescence responses produced by plural, "attached-to" oligonucleotide probes disposed within a specific pixel during a DNA assay.

It should be apparent that functionalizer structure 14b and optical detector structure 14c have been illustrated each with three substructures simply for illustrative purposes herein, and not with any intention to limit the notion that a different plural number of such sub-functionalizers and sub-detectors could be employed if desired.

Employing the same reference numerals and characters which are used in FIG. 1 for like structure, FIG. 2 illustrates that embodiment, or modification, of the invention wherein the individual pixels in array 11 do not include pixel-specific optical detectors (such as that detector which is referenced at 12c in FIG. 1). In all other respects, the structural arrangement shown in FIG. 2 is like that which is illustrated in FIG. 1.

What has thus been described so far are the structures and the makings of several different versions of a pixelated, DNA-assay, micro-structure array to the point where the pixels in that micro-structure have been brought to what has been referred to herein as precursor, or not-yet-functionalized, conditions—readied for the eventual fabrication, on the described hosting sites, of oligonucleotide probes which may then be used to implement a DNA assay. Such an array, with its pixels in non-functionalized, precursor states, is poised for the final creation of same, or different, selected oligonucleotide probes. Such a precursor array obviously has significant utility in terms of its being a product readied for a user to create a finalized, functionalized version having the desired oligonucleotide probes. As will now be explained, individual pixel energizing and operating of the various pixel-specific functionalizers affords the opportunity for the selective creation of a finalized-condition, fully functionalized DNA assay micro-structure, as will shortly be explained.

One comment which should be made at this point, before describing next the practice of functionalization, is that, while the most prevalent manner for creating oligonucleotide probes involves the use of an energizing light source for functionalizing each pixel, one should recognize that it is entirely possible to create a unique micro-structure array, such as the one so far described herein, wherein some form of energy other than light, such as heat-field energy or defined electrical-field energy, might be a medium employable successfully in the functionalizing process, as well as in an assay-result output-reading procedure. Accordingly, it should be understood that while the preferred embodiments and manners of making, a micro-structure DNA assay array as so far described herein speak in terms of light-based functionalizers, the term "functionalizer" could refer to any other appropriate energizable, energy-field-producing structure, pixel-specific in nature, which might be employed to perform functionalization. Those skilled in the art will recognize that such other-style functionalizers could easily be fabricated as pixel-specific, pixel-incorporated devices in a pixelated array as contemplated by the present invention.

Focusing now on the operation and utility of each pixel-specific functionalizer with respect to how that functionalizer plays a unique and important role in finalizing/functionalizing the structure of a pixel by aiding in the creation of an associated DNA oligonucleotide probe on an associated hosting site for that probe, the functionalizer, during a step-by-step building process for creating that probe, is selectively energized recurrently (i.e., sequentially, and in a step-by-step fashion) during probe fabrication to shine light into the region which will be occupied by the probe. In relation to this probe-fabrication process, two prior art patents—U.S. Pat. No. 5,143,854 to Pirrung, U.S. Pat. No. 6,280,595 B1 to Montgomery, and U.S. Pat. No. 6,985,665 B2 to Yamamoto—provide excellent and relevant background information regarding the traditional optico-chemical building of an oligonucleotide probe. Accordingly, the full disclosure contents of these three patents are hereby incorporated herein by reference. These patents fully describe the basic probe-formation procedure which is implemented in the functionalization practice of the present invention, with the significant exception of how light energy is utilized to create the required, sequential, fabrication steps known as "deprotection" steps. Such deprotection steps are employed to expose the outer ends of emerging-probe components so as to enable the attachment thereto of a next probe component.

As will be observed from a reading of these three patents, it is typical that a flow-cell approach is employed to create oligonucleotide probes in an assay structure. In this approach, relevant DNA-associated flow material is passed, in a staged manner, through a flow cell, and over the associated flow-cell-contained and exposed, pixelated assay structure. This staged material-flow practice is combined procedurally with the stage-interspersed shining of light of an appropriate wavelength and power level, directed, from completely outside the employed flow cell (i.e., from a location, or locations, that is/are remote from the subject, flow-cell-contained assay structure) to perform, at the appropriate times, the just-above-mentioned, sequential deprotection steps as, i.e., before, each new organic component which is to be employed and added in the creation of a particular oligonucleotide probe is thereafter made available for probe attachment to an emerging probe.

Thus, in substantially each traditional building step of the described probe-fabrication process, and following a completed "probe-outer-end" (i.e., outer terminus/extremity) deprotection operation which exposes, for attachability thereto, the relevant, functional outer extremity of the then outer component in an emerging probe, an appropriate, next component of an oligonucleotide probe becomes flow-cell-enabled attached to the thus-deprotected outer-extremity component. Once attached, and assuming that at least one additional probe component is next to be added, that just last-attached component, which, naturally and intentionally, carries at its outer terminus a suitable "protection" element, is subjected at that outer terminus to a deprotection step which is implemented again by a remote light source, the action of which removes terminus protection so as to poise the terminus of the still-emerging probe for the attachment of the next-desired sequential probe component.

Somewhat similar flow-cell technology is preferably employed during practice of the present invention in the building of oligonucleotide probes in a micro-structure array made in accordance with the invention.

Beginning with an initial yet-unfunctionalized, substrate-supported precursor array of pixels, single-strand oligonucleotide probe-building on the appropriate pixel hosting sites is launched in a flow-cell setting of the type just mentioned above, wherein the pixel-array-bearing face of the associated supporting substrate forms one inwardly facing side of an otherwise conventional flow-cell structure, through which structure successive, staged flows of relevant, probe-building, organic-content fluids are produced during the probe-building process. With respect to these successive flows, and with the important exception, mentioned generally above herein, of how light is used to implement otherwise conventional deprotection steps that are required to effect stage-by-stage organic chemical reactions in the building of a probe, the building process may be entirely conventional, and in fact may be carried out, if desired, utilizing specifically any one of the various probe-building approached described in the three, above-referenced U.S. Patents.

During this probe-building process, deprotection, when and where required, including at the start of the process with regard to the "starter" probes created during pixel functionalization, is performed by addressably energizing the appropriate, fully selectable and individually addressable pixel functionalizers whose pixel-specific light outputs invoke the required deprotection at the outer extremities of the then-forming, associated oligonucleotide probes. Appropriate organic DNA flow-fluid is then passed through the relevant flow cell, new-component attachments take place at the specifically "deprotected" probe outer ends, and following such attachments, and as appropriate, next-sequential stages of deprotection and fresh-component attachment are performed.

Thus the preliminary-context methodology of the present invention, and the resulting initially-produced precursor structure, afford an extraordinary level of ease and pixel-by-pixel control over the ultimate building of versatile and useful DNA oligonucleotide probes. This, among other reasons, is because of the facts that, in accordance with practice of the present invention, (a) each pixel is fully, individually addressable under the control of an external instrumentality, such as a computer, and (b) is thereby equipped with an individuated, pixel-specific functionalizer/energizer which allows, thereafter, for pixel-by-pixel fabrication of an oligonucleotide probe in that pixel independently of the fabrication of any other such probe on any other pixel.

This high degree of pixel-addressable, pixel-specific, active-matrix control offers extraordinary versatility in the structuring of a fully functionalized micro-structure assay array, and, among other things, allows for the very easy fabrication of pixelated arrays wherein different pixels may be sensitized differently by possessing different probes, and also whereby a user of the present invention can control completely and accurately the deployment pattern of oligonucleotide probes. Each embodiment of the invention illustrated and described herein, as will be clearly apparent to those skilled in the art, enables, because of pixel-specific addressability, the opportunity to create a wide variety of accurately controlled and structured pixel arrays in relevant micro-structure arrays.

A very important consequence of this easily implemented pixel-differentiation capability is that various "broad-band-functional" arrays can be constructed readily and quickly. Relevant pixel differentiation for such broad-band functionality can be implemented in many different ways. For example, different pixels may each include a single probe site and a single functionalizer with respect to which certain probes may be functionally differentiated selectively from other probes. Also, different pixels may be fabricated to possess (a) different numbers of probe sites, and/or (b) differently operable functionalizers (i.e., functionalizers operable with different functionalizing energy characteristics, as suggested earlier herein) thus to permit probe-functional differentiation on both inter-pixel and intra-pixel bases.

Another interesting possibility involves preparing a micro-structure DNA assay array which offers plural, successive use capabilities. As an illustration, not all pixels in an array need necessarily have their respective "starter", functionalized probes fully "armed", so-to-speak, at the same time for an assay. Thus, an array could, over time, be employed several times, with different probes in the pixels being selectively poised for assay behavior in each different one of plural assays.

Turning attention now to use of a DNA assay micro-structure made in accordance with the present invention, another very unique aspect of the invention is that the functionalizers in an array of pixels may be addressably energized individually and selectively to illuminate probe sites during a DNA assay, thus to prompt related fluorescence-response behavior as part of a DNA assay. Such response-prompting light-field illumination can be performed substantially instantly under the control of an appropriate addressing computer, such as computer 28.

Where, as in the preferred embodiment of the invention, each pixel also includes a fully integrated, pixel-specific optical detector of appropriate construction, this detector may be employed to provide such a computer immediately with an unambiguous, pixel-specific output signal which is directly indicative of pixel-specific fluorescence-response triggered in the associated DNA probe.

Further, the assay micro-structure of the present invention allows for the very unique practice of detecting kinetic characteristics, if any, of a probe's response by "interrogating" that response via repetitive, time-sequential computer "looks" at the output signal produced by the relevant, associated optical detector. Those skilled in the art will recognize that, via a combination of (a) selective pattern and style (nature) of functionalization, and (b) time-based repetitive output signal-inquiring, a great deal valuable DNA assay information not heretofore available in the practices offered by the prior art may be obtained.

In relation to the methodology contributions made to the art by the present invention, these contributions are expressible in different ways regard to different methodologic facets of the invention. One of these ways, from a high-level perspective, takes a view of the invention as a method for making a fluid-assay, active-matrix micro-structure in the form of a plural-pixel-site array on a supporting substrate (preferably glass or plastic) including the steps of (a) specifying and producing such a plural-pixel-site array and the pixel sites therein, and (b) with respect to each such pixel site, and preferably utilizing low-temperature TFT processing as described above, creating a pixel-site-specific, externally and individually addressable, selectively energizable, energy-field-producing oligonucleotide probe functionalizer on the site. An augmentation of this view includes the additional step of establishing an output-producing, fully pixel-integrated optical detector disposed within each specified and produced pixel site.

Another methodology view of the invention involves describing the invention as a method of making a fluid-assay, active-matrix micro-structure on a supporting (preferably glass or plastic) substrate including (a) specifying and producing a pixel site on the substrate, and (b) with respect to that site, creating an externally and individually addressable, selectively energizable light source on the site.

From still a further and different-facet view of the invention, it can be described as a method for performing a DNA assay utilizing a substrate-supported, pixelated, fluid-assay, active-matrix micro-structure which includes an array of externally digitally-addressable pixels, each of which is defined by pixel-incorporated, pixel-specific structure including (a) at least one functionalized DNA oligonucleotide probe operable to exhibit an optical response during a relevant DNA assay, (b) at least one addressable and energizable optical-illumination functionalizer which was energized to functionalize the at least one probe utilizing optical illumination, and (c) at least one addressable optical detector operatively and optically associated with the probe, operable to produce an electrical output signal in relation to any optical response exhibited by the probe during a DNA assay, with the steps of the method including (a) exposing probes in the pixels to relevant DNA assay material, and (b) following such exposing, and on a pixel-by-pixel basis, addressably reading the respective, probe-associated detectors to observe any output signals produced by thereby.

It is thus the case that a very useful precursor structure may be made in accordance with the present invention including pixels in an array which can be oligonucleotide-probe-functionalized in a variety of different configurations, and on a pixel-by-pixel-addressable basis utilizing pixel-on-board functionalizers, preferably optical in nature. Such a device offers a user wide and versatile latitude in final user-preparation of a fully functionalized DNA assay micro-structure. Where each pixel also includes an optical output detector, output information can be derived, preferably, pixel-by-pixel through addressably examining any responses which are produced by pixel-associated optical output detectors. Such responses can be elicited utilizing illumination sourced from the very functionalizers which aided in the practice of building functionalized oligonucleotide probes, per se.

Those skilled in the art will surely recognize that if it turns out to be the case that a functionalizer/field-creator operating at one wavelength is what is required for probe-fabrication purposes, and another-wavelength illuminator is required to trigger fluorescence behavior as an output part of a DNA assay, it is entirely possible to build a pixel in accordance with practice of the present invention to include another pixel-like functionalizer/illuminator which operates at an appropriate output-signal-triggering wavelength.

With respect to an embodiment of the invention which is constructed as shown in FIG. 2, wherein the individual pixels in an array do not possess optical output detectors, assay probe output responses, such as fluorescence responses, may be observed in any suitable conventional way. Additionally, the structure of the present invention offers a user the special opportunity to examine the kinetic, time-based natures of probe responses to DNA assay material.

With these unique features made possible by the individually addressable pixel structure proposed by the present invention, it is easy to understand how the described structure and methodology of the present invention successfully addresses the several drawbacks associated with prior art structures mentioned earlier herein. Following a DNA assay, and because of pixel-by-pixel addressability, there can be no mistaking which probes on which pixels give a fluorescence behavior when properly illuminated by the associated, preferably optical functionalizers.

The matrix structure made by practice of the invention preferably utilizes a low-cost substrate material, such as glass or plastic, and features the low-temperature fabrication on such a substrate of supported pixel structures, including certain kinds of special internal components or substructures, all formed preferably by low-temperature TFT and Si, etc. technology as discussed above.

Accordingly, while a preferred and best mode form of the invention, and certain modifications thereof, have been illustrated and described herein, additional variations and modifications may also be made which will come within proper spirit and scope of the invention.

We claim:

1. An active-matrix, thin-film-transistor-based, DNA fluid-assay micro-structure comprising a substrate having a face, plural pixels formed in common on said substrate's said face in the arrangement of a matrix, and within, as an included part of, each pixel on said face, (a) at least one initially non-functionalized, DNA oligonucleotide-probe-lacking, assay site, and (b), disposed on said face, laterally adjacent said site, (1) a thin-film energizing transistor, and (2) an energizable, light-field-creating functionalizer operatively connected to, and energizable by, said transistor, and whose created light field, when created via associated transistor energizing, is operable to functionalize the pixel by participating in the building, from a precursor condition of the pixel, of a DNA oligonucleotide probe on said at least one site.

2. The micro-structure of claim 1, wherein said substrate is formed of low-temperature glass or plastic.

* * * * *